(12) United States Patent
Bulut et al.

(10) Patent No.: US 11,529,105 B2
(45) Date of Patent: Dec. 20, 2022

(54) DIGITAL TWIN UPDATING

(71) Applicant: KONINKLIJKE PHILIPS N.V., Eindhoven (NL)

(72) Inventors: Murtaza Bulut, Eindhoven (NL); Valentina Lavezzo, Heeze (NL); Cornelis Petrus Hendriks, Eindhoven (NL); Lieke Gertruda Elisabeth Cox, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 224 days.

(21) Appl. No.: 16/843,261

(22) Filed: Apr. 8, 2020

(65) Prior Publication Data

US 2020/0330046 A1     Oct. 22, 2020

Related U.S. Application Data

(60) Provisional application No. 62/834,713, filed on Apr. 16, 2019.

(51) Int. Cl.
*A61B 5/00* (2006.01)
*G16H 50/50* (2018.01)
(Continued)

(52) U.S. Cl.
CPC .......... *A61B 5/7275* (2013.01); *A61B 5/7264* (2013.01); *G16H 10/60* (2018.01);
(Continued)

(58) Field of Classification Search
CPC ... A61B 5/0022; A61B 5/0205; A61B 5/6801; A61B 5/7264; A61B 5/7275;
(Continued)

(56) References Cited

U.S. PATENT DOCUMENTS 8,620,591 B2    12/2013  Wegerich
2013/0325493 A1*  12/2013  Wong ..................... G16Z 99/00
                                                             705/2
(Continued)

OTHER PUBLICATIONS

Y. Liu et al., "A Novel Cloud-Based Framework for the Elderly Healthcare Services Using Digital Twin," in IEEE Access, vol. 7, pp. 49088-49101, 2019, doi: 10.1109/ACCESS.2019.2909828. (Year: 2019).*

(Continued)

*Primary Examiner* — Jennifer Pitrak McDonald
*Assistant Examiner* — Shreya Anjaria (57) ABSTRACT

Disclosed is a method (100) of providing a personalized parameter model of at least part of the physiology of a person (10) carrying a set of sensors (12, 14, 16) with a computer system (20, 50) comprising a processor arrangement (22, 52) for the purpose of updating a biophysical model or digital twin of the person. The method comprises, with said processor arrangement, receiving (103) sensor data from said set of sensors with the communication interface over a defined period of time, the sensor data from each sensor representing a parameter relevant to an actual physiological state of the person; evaluating (105) the received sensor data from each sensor to define the personalized parameter model (3), said model including the evaluated dynamic behaviour of the values of each parameter observed with said sensors over the defined period of time and providing (107) the defined personalized parameter model for updating a digital model (1) of at least part of the anatomy of said person. Also disclosed is a method (200) for updating such a digital twin in which the digital twin is updated using such a personalized parameter model. In addition, a computer program product for implementing such methods and a computer system (20) implementing such methods are also disclosed.

14 Claims, 7 Drawing Sheets

(51) Int. Cl.
  *G16H 50/20* (2018.01)
  *G16H 50/30* (2018.01)
  *G16H 10/60* (2018.01)

(52) U.S. Cl.
  CPC ............ *G16H 50/20* (2018.01); *G16H 50/30* (2018.01); *G16H 50/50* (2018.01)

(58) Field of Classification Search
  CPC ........ G16H 10/20; G16H 10/60; G16H 40/63; G16H 50/20; G16H 50/30; G16H 50/50
  See application file for complete search history.

(56) References Cited

U.S. PATENT DOCUMENTS

| | | | |
|---|---|---|---|
| 2014/0172459 A1 | 6/2014 | De Vries et al. | |
| 2017/0177822 A1* | 6/2017 | Fogel | G16H 50/20 |
| 2017/0286572 A1 | 10/2017 | Dell'Anno et al. | |
| 2018/0325460 A1* | 11/2018 | Wegerich | A61B 5/0205 |
| 2019/0252079 A1* | 8/2019 | Constantin | A61B 5/0024 |
| 2020/0012959 A1 | 1/2020 | Karanam et al. | |
| 2020/0129066 A1* | 4/2020 | Gedamu | A61B 5/002 |

OTHER PUBLICATIONS

Neal ML, Kerckhoffs R. Current progress in patient-specific modeling. Brief Bioinform. 2010;11(1):111-126. doi:10.1093/bib/bbp049 (Year: 2010).*
Diaz, V., https://www.wareable.com/health-and-wellbeing/doctor-virtualtwin-digital-patient-ucl-887.
Neal, M.L. et al. "Current progress in patient-specific modeling". Briefings in Bioinformatics. (2009), vol. 2, pp. 111-126.

* cited by examiner

DIGITAL TWIN UPDATING

CROSS-REFERENCE TO PRIOR APPLICATIONS

This patent application claims the priority benefit under 35 U.S.C. § 119(e) of U.S. Provisional Application No. 62/834,713, filed on Apr. 16, 2019, the contents of which are herein incorporated by reference.

FIELD OF THE INVENTION

The present invention relates to a method of updating a digital model of a person such as a patient using one or more sensors monitoring this person.

The present invention further relates to a computer program product for implementing such a method.

The present invention further relates a computer system arranged to implement such a method.

BACKGROUND OF THE INVENTION

In many developed countries, the provision of healthcare is becoming increasingly strained. Some reasons for this include the growth of the population and increasing life expectancy. Unfortunately, although people live longer, the average age at which their health deteriorates to the point where regular medical care is required is not increasing accordingly, such that the ageing population is unwell for longer, which increases the pressure on the healthcare system, e.g. on medical practitioners, medical infrastructures such as hospitals, diagnostic equipment therein, and so on. Hence, rather than simply increasing medical resources, for which the financial resources may not be available, there exists a need to improve the efficiency of such healthcare systems.

A recent development in technology is the so-called digital twin concept. In this concept, a digital representation (the digital twin) of a physical system is provided and connected to its physical counterpart, for example through the Internet of things as explained in US 2017/286572 A1. Through this connection, the digital twin typically receives data pertaining to the state of the physical system, such as sensor readings or the like, based on which the digital twin can predict the actual or future status of the physical system, e.g. through simulation, as well as analyze or interpret a status history of the physical twin. In case of electromechanical systems, this for example may be used to predict the end-of-life of components of the system, thereby reducing the risk of component failure as timely replacement of the component may be arranged based on its end-of-life as estimated by the digital twin.

Such digital twin technology is also becoming of interest in the medical field, as it provides an approach to more efficient medical care provision. For example, the digital twin may be built using imaging data of the patient, e.g. a patient suffering from a diagnosed medical condition as captured in the imaging data.

Such a digital twin may serve a number of purposes. Firstly, the digital twin rather than the patient may be subjected to a number of virtual tests, e.g. treatment plans, to determine which treatment plan is most likely to be successful to the patient. This therefore reduces the number of tests that physically need to be performed on the actual patient. The digital twin of the patient for instance further may be used to predict the onset, treatment or development of such medical conditions of the patient using a patient-derived digital model, e.g. a digital model that has been derived from medical image data of the patient. In this manner, the medical status of a patient may be monitored in a smarter manner, with a more efficient involvement of a medical practitioner, e.g. avoiding unnecessary periodic routine physical checks of the patient. Instead, only when the digital twin predicts a medical status of the patient indicative of the patient requiring medical attention based on the received sensor readings may the digital twin arrange for an appointment to see a medical practitioner to be made for the patient, for example. This therefore helps to minimize cost, improve patient and practitioner satisfaction.

This typically also leads to an improvement in the medical care of the patient, as the onset of certain diseases or medical conditions may be predicted with the digital twin, such that the patient can be treated accordingly at an early stage, which not only is beneficial to the patient but can also reduce (treatment) costs. Moreover, major medical incidents that the patient may be about to suffer may be predicted by the digital twin based on the monitoring of the patient's sensor readings, thereby reducing the risk of such incidents actually occurring. Such prevention avoids the need for the provision of substantial aftercare following such a major medical incident, which also alleviates the pressure on a healthcare system otherwise providing such aftercare.

Such remote monitoring of a patient may lead to an infrequent need for the patient to physically meet a healthcare professional. However, a drawback of this approach is that such a digital model at least initially may present a rather incomplete or inaccurate model of the actual patient due to the limited data on which the digital model is based. Hence, there exists a need to update the digital model or at least the procedures leading to its updating at certain times without such a patient having to be subjected to tests in a controlled environment such as a doctor's surgery or a medical clinic such as a hospital.

SUMMARY OF THE INVENTION

The present invention seeks to provide a method for updating a digital model of a person without the person having to visit a medical facility or the like for this purpose.

The present invention further seeks to provide a method of updating a digital model with data provided by the aforementioned method.

The present invention further seeks to provide a computer program product for implementing at least one of these methods.

The present invention further seeks to provide a computer system arranged to implement at least one of these methods.

According to an aspect, there is provided a method of providing a personalized parameter model of at least part of the physiology of a person carrying a set of sensors with a computer system comprising a processor arrangement, the method comprising, with said processor arrangement, receiving sensor data from said set of sensors with the communication interface over a defined period of time, the sensor data from each sensor representing a parameter relevant to an actual physiological state of the person; evaluating the received sensor data from each sensor to define the personalized parameter model, said model including the evaluated dynamic behaviour of each parameter observed with said sensors over said defined period of time; and providing the defined personalized parameter model for updating a digital model of at least part of the anatomy of said person.

The present invention is based on the insight that sensor data collected from such a person outside a controlled test environment can still be used to validate the test protocols and actual digital model of (part of) the anatomy of the person. In other words, sensor data collected from the person during daily life can be used to check if the test protocols for updating the digital model or indeed the digital model itself are still up to date. This for instance can be checked by evaluation of the dynamic behaviour of the values for the monitored parameters, such as for example changes in values over time, rate of change of such values, and so on, which evaluated dynamic behaviour can provide useful information as to the actual physiology of the person. Such dynamic behaviour may be linked to lifestyle information derived from the sensor data or as provided by the user in order to define a set of transfer functions in which a particular lifestyle event, e.g. an activity or the like, of this person can be translated into a (change in) dynamic behaviour of at least some of the physiological parameters of interest. In this manner, the digital model (digital twin) of the person can be kept up to date without the person necessarily requiring visiting a medical facility in order for one or more controlled tests to be performed to obtain the dynamic behaviour of such parameters for instance, e.g. because the digital model may be updated using the observed dynamical behaviour of and/or derived transfer functions from the observed parameters.

The evaluation of the received sensor data from each sensor to define the personalized parameter model may further comprise determining the end points of a parameter value range for each parameter based on the values of each parameter observed with said sensors over the defined period of time; and including said determined end points in the personalized parameter model. The determination of the end points of such ranges, for instance facilitates the checking at the location of the implementation of such test protocols and/or digital model if this full range is (still) covered in its entirety by the test protocols and/or digital model or if an update of the test protocols and/or digital model is required instead. In this manner, the digital model can be kept up to date without the person necessarily requiring visiting a medical facility in order for one or more controlled tests to be performed to obtain the end points of such a parameter value range with greater accuracy for instance. The end points of such a range may correspond to the actually observed values of the parameter. Alternatively, at least one of the end points may be extrapolated from the observed values, for example where the observed parameter values are indicative of a particular physical condition of the person, such that such an end point of the range for such a parameter may be based on an end point value that is typical for the indicated physical condition.

In a preferred embodiment, evaluating the received sensor data from each sensor to define the personalized parameter model further comprises dividing the observed parameter values of at least some of the parameters into a plurality of clinically relevant sub-ranges; generating a distribution of the observed parameter values across the plurality of clinically relevant sub-ranges; and including said distribution in the personalized parameter model. Such sub-ranges, or clusters, of parameter values for example may be used to clinically classify the observed parameter values, e.g. as 'below ideal/normal', 'ideal/normal' and 'above ideal/normal', or 'ideal/normal', 'moderately high', 'very high' and so on, which can provide a more detailed insight in the physiological condition of the person over the monitoring period, for example by evaluating how many actual data points are contained in each of the sub-ranges. In addition, such an evaluation may further include information pertaining to the time it takes a parameter to reach a value within a certain sub-range, the time it takes a parameter value to move between sub-ranges, interrelationships between parameters that are specific to certain sub-ranges, which can provide further useful information about the person's physiology and physical condition.

Evaluating the received sensor data from each sensor to define the personalized parameter model may comprise determining relationships between said parameters and including the determined relationships in the personalized parameter model. Such relationships for instance may be derived from related trends in the values of such parameters and may provide useful insights in how to update the digital model of the patient such that the digital model can more accurately simulate the person's physiology.

In a further embodiment, the method further comprises receiving at least one of activity information and psychological information for a particular point in time for said person; associating received sensor data acquired at that particular point in time with said received information and including said associations in the personalized parameter model. This provides further useful insights into the factors that affect the physiology of the person, which therefore can be leveraged to further improve the accuracy of the digital model.

According to another aspect, there is provided a method for updating a digital model of a person carrying a set of sensors with a computer system comprising a processor arrangement under control of the processor arrangement, wherein each sensor in said set of sensors is arranged to collect sensor data representing a parameter relevant to an actual physiological state of the person; and the digital model is a parameterized model based on at least some of the parameters sensed with said set of sensors; the method comprising, with said processor arrangement, obtaining the personalized parameter model provided in accordance with the method of any of the herein described embodiments; and updating the digital model using the personalized parameter model.

In this manner, the digital model may be validated and if necessary updated using relevant (sensor) data obtained from the person during his or her daily activities without this person necessarily having to visit a medical facility for such validation purposes, as previously explained.

It is noted at this point that where reference is made to updating the digital model, that such updating refers to changing the digital model such that the digital model more closely reflects or is better capable of simulating the physiology of at least part of the anatomy of the person, e.g. an organ model, a cardiovascular model, a pulmonary model, and so on. Hence, such updating is not intended to merely reflect performing a simulation with an existing digital model but rather is intended to cover changes to the digital model that typically influence the outcome of such simulations, such as for example changes to one or more of the algorithms, settings or other building blocks of such a digital model that are used to perform such simulations. This may also be referred as training the digital model. Additionally, the personalized parameter model may be used to alter the way the output of the digital model is presented and visualized. In the context of the present application, updating a digital model is further intended to cover the creation of a digital model.

In one embodiment, the method comprises comparing the determined dynamic behaviour of each parameter observed with the set of sensors with a previously assumed dynamic behaviour of said parameter on which the digital model is based, and if the determined dynamic behaviour of at least one parameter observed with the set of sensors is different to the previously assumed dynamic behaviour of said parameter: updating a test protocol for obtaining the dynamic behaviour of said parameter in a controlled test performed on the person; and updating the digital model with the dynamic behaviour of said parameter as obtained from said person in said controlled test. This for instance is beneficial where the dynamic behaviour of the parameter obtained from the sensors monitoring the person cannot be directly used to update the digital model, for example because the accuracy of such data is such that verification of these values is desirable, because the data is not in an appropriate format or because the data cannot be used for such purposes, e.g. because of digital rights issues. In such a scenario, the parameters may be used to configure a controlled test in such a manner that the full range and distribution of expectation values for the parameter of interest as well as interrelations between parameters and their dynamic behaviour where appropriate can be captured by such a test. In the context of the present invention, a controlled test may be a test for which the accuracy of the resulting parameter values is sufficient to be used to directly update the digital model where necessary. For example, tests performed in a hospital or a comparable medical facility, that is, tests that are performed by trained medical staff using calibrated equipment, are typically considered controlled tests.

In another embodiment, updating the digital model using the personalized parameter model comprises directly updating the digital model with the dynamic behaviour of said parameter observed with a sensor from the set of sensors. This may be advantageous where such data is difficult to obtain in controlled tests, for example where such data should be captured over a relatively long period of time such that the required variability in the data to update the digital model is captured, or where the data is required to test the robustness of the digital model for real-life conditions of the person.

The method may further comprise validating the digital model using the dynamic behaviour of at least one of the parameters observed with the set of sensors, for example by testing the existing digital model to see if the digital model is capable of reproducing the full dynamic behaviour of the sensed parameters as well as interrelations between parameters and their dynamic behaviour where appropriate, which provides an indication of whether the digital model requires updating.

In a further embodiment, the method further comprises generating a further personalized parameter model comprising a further dynamic behaviour of the sensed parameters with the updated digital model; comparing the further personalized parameter model with the personalized parameter model; and if the further personalized parameter model differs from the personalized parameter model, further updating the digital model based on said determined difference. In this manner, the quality of any update of the digital model can be verified, thereby facilitating further improvement of the digital model in an iterative manner.

In yet another embodiment, the method further comprises determining a set of behaviours of a person that each cause a trend in a value of at least one parameter on which the digital model is based; running a simulation with the digital model using the behaviours in said set and optionally at least one of historical parameter data and parameter data from the personalized parameter model associated with behaviours in said set as input data; evaluating said simulation; and generating a behavioural model of the person comprising each of the behaviours in said set identified by the simulation evaluation as relevant to the person. Such a behavioural model, which may be generated for example by using an information database or the like, may contain certain types of behaviour including activities that cause certain trends in relevant parameter values. Hence, such a behavioural model may be used to link observed trends in the parameter values obtained with the sensors to certain behaviours, which information may be used to more accurately update the digital model, for example.

In addition, such a behavioural model may be used to train the person to avoid such behaviours, or at least manage them in a healthier way, where such behaviours cause potentially health-threatening trends in the physiology of the person as observed with the sensed parameters. To this end, the method may further comprise receiving a subsequent personalized parameter model based on a subsequently determined range of values for each parameter observed with said set of sensors; evaluating the received subsequent personalized parameter model for a trend in the sensor data of the subsequent personalized parameter model that corresponds to one of the behaviours in the behavioural model with the digital model; and generating an electronic message for the person if the evaluation of the received subsequent personalized parameter model identifies a trend in the sensor data of the subsequent personalized parameter model that corresponds to one of the behaviours in the behavioural model with the digital model, said electronic message containing information for the user pertaining to the identified behaviour.

Such information may be further based on received activity information and/or psychological information for said person that is relevant to the identified trend in the sensor data, in which case the information in the electronic message may alert the person to the relevance of his or her daily living activities and/or psychological state to their physiology, such that the person may try to address such behaviour accordingly. The information in the electronic message may further provide the person with advice as to how to avoid or limit the impact of such behaviour, or more generally, how to manage such behaviour in a responsible manner.

According to another aspect, there is provided a computer program product for a computer system comprising a processor arrangement, the computer program product comprising a computer readable storage medium having computer readable program instructions embodied therewith for, when executed on the processor arrangement, cause the processor arrangement to implement one or more of the methods of any of the herein described embodiments. Such a computer program product for instance may be used to configure existing computer systems to implement the method according to embodiments of the present invention.

According to yet another aspect, there is provided a computer system comprising a processor arrangement, wherein the processor arrangement is adapted to implement one or more of the methods of any of the herein described embodiments. For example, the processor arrangement may be hard-coded to implement such a method or alternatively the computer system may further comprise the computer program product according to any of the herein embodiments of the present invention. Such a computer system may be used to validate a digital model of a person without the need for such a person to be necessarily subjected to controlled tests such as in a medical facility as explained in more detail above.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

Figure 1:
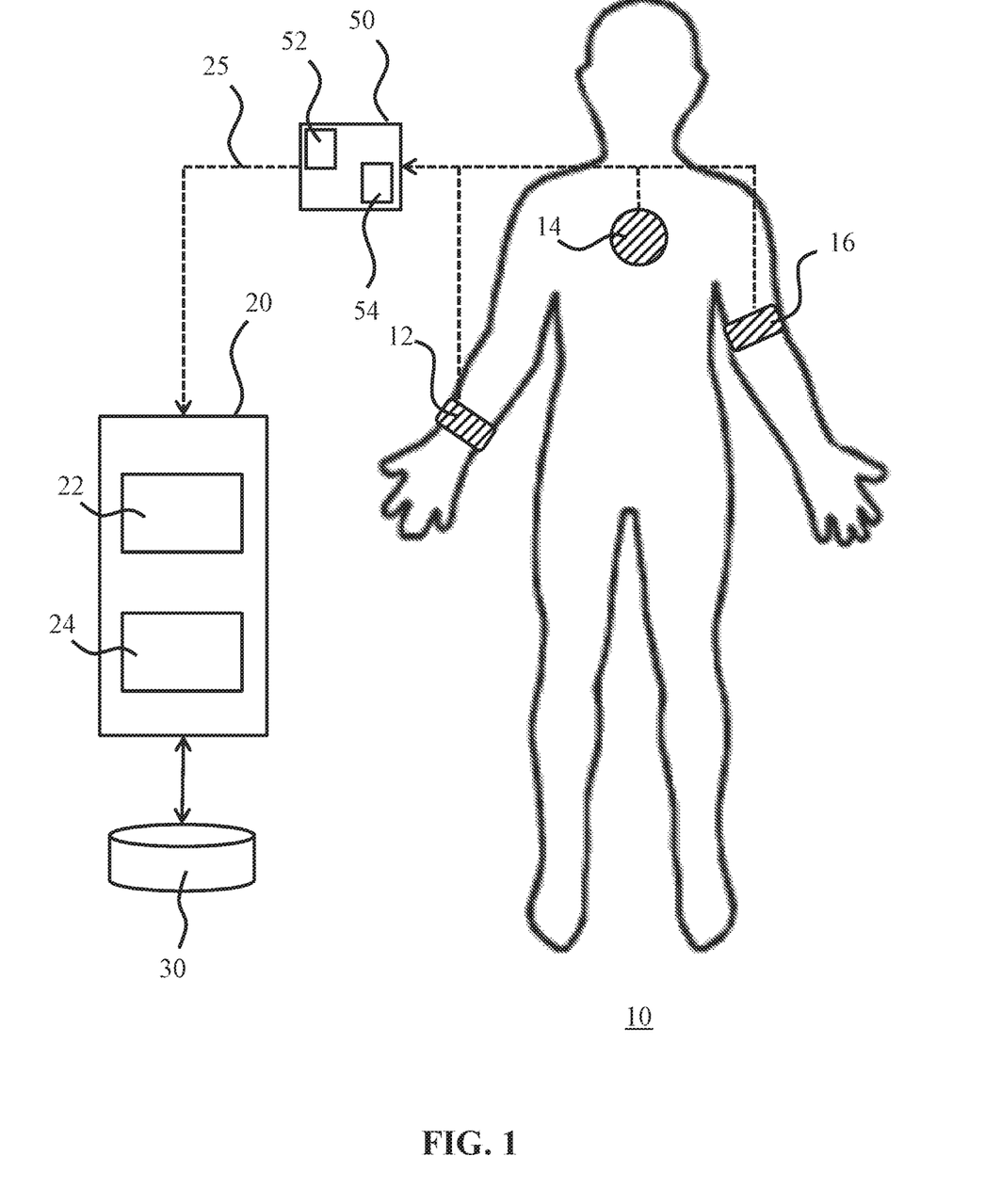
FIG. 1 schematically depicts a monitoring environment of a person having a digital twin according to an embodiment.

FIG. 1 schematically depicts a generalised setup to which embodiments of the present invention are applicable. A person such as a patient 10 is monitored by one or more sensors, here schematically depicted by sensors 12, 14 and 16 by way of non-limiting example only, which one or more sensors are arranged to provide sensor data to a computer system 20 comprising a processor arrangement 22 and a data communication module 24 to which the one or more sensors are communicatively coupled through a data link 25. The one or more sensors may be directly linked to the computer system 20 or alternatively may be connected to a relay device 50 that collects the sensor signals and relays these signals to the computer system 20 over the data communication link 25 using its data communication module 54. The relay device 50 typically further comprises a processor arrangement 52, which may control the data communication module 54 and may further be arranged to perform some processing on the received sensor data prior to this data being forwarded to the computer system 20. Such a relay device 50 may be a computer system in its own right, and in preferred embodiments may be a portable electronic device such as a dedicated sensor data relay device, a portable communication device such as a smart phone, a tablet or laptop computer, and so on.

The processor arrangement 22 of the computer system 20 may take any suitable shape. In the context of the present invention, a processor arrangement may comprise one or more processors, processor cores and the like that cooperate to form such a processor arrangement. Similarly, the data communication module 24 and the data communication module 54 may take any suitable shape, such as a wireless or wired data communication module, as is well known in the art and will therefore not be further explained for the sake of brevity only.

The data link 25 may take any suitable shape, such as a wireless communication link, a wired communication link or a combination thereof. Any suitable communication protocol may be deployed between the one or more sensors and the communication module 24, or between the data communication module 24 and the data communication module 54 over the data link 25. For example, in case of a wireless communication link, the communication protocol may be Wi-Fi, BLUETOOTH® wireless technology communication protocol, a mobile phone communication protocol such as 3G, 4G, 5G and so on. Other examples of suitable wireless communication links will be immediately apparent to the skilled person. In case of a wired communication link, suitable application protocols may include TCP/IP and similar protocols used to communicate over a wired data communication link such as a wired network, e.g. the Internet.

The computer system 20 is typically remote from the person 10 such that the person 10 may be monitored from a distance. This allows for the monitoring of the person 10 during his or her daily activities, without such a person 10 having to be subjected to controlled tests in a hospital environment or the like to obtain values for the parameters monitored with the sensors 12, 14, 16. For example, the computer system 20 may comprise a remote server or the like on which the digital twin of the patient 10 is hosted.

The one or more sensors typically are each arranged to monitor a physiological parameter of the person 10. Such parameters are typically indicative of a physical condition of the person 10. The one or more sensors 12, 14, 16 may be wearable sensors, e.g. battery-powered wearable sensors, epidermal sensors and/or may be sensors implanted or otherwise temporarily or permanently into the body of the patient, which typically are also battery powered sensors. Moreover, such sensors do not need to be in physical contact with the person 10. For example, sensors in the environment of the person 10 or in electronic devices used by the person 10 may also monitor such physiological parameters. Such sensors 12, 14, 16 may electrically, mechanically, thermally, chemically or optically measure digital signal and parameters of the person 10 from which physiological indicators such as temperature, heart rate, blood pressure, blood flow rate, fractional flow reserve, respiration rate, blood chemistry such as blood glucose level, sweat levels, brain activity (EEG), motion, muscle activity, speech, image-based monitoring (e.g. to monitor body regions of the patient) and so on can be calculated or estimated. Other physiological parameters that may be monitored with such sensors include blood glucose levels, bladder fill levels, blood flow rates, e.g. using Doppler ultrasound sensors, and so on. The skilled person will understand that the teachings of the present application are not limited to a particular type of sensor and may be any type of sensor that can be used to monitor any useful physiological parameter of the person 10. In addition, any of the sensors 12, 14, 16 may comprise a user interface allowing the user to provide relevant input data to supplement the sensor data of such a sensor.

The computer system 20 may be communicatively coupled to a data storage device 30, which may store a digital model of the person 10. Any suitable type of data storage device 30 may be used for this purpose, such as a data storage device 30 forming part of the computer system 20, or a data storage device 30 that is accessible by the computer system 20 over a network such as a storage area network (SAN) device, a network attached storage (NAS) device, a cloud storage device, and so on. Such a digital model in the remainder of this application will also be referred to as a digital twin of the person 10. The digital twin hosted by the computer system 20 typically provides at least one of a data-driven model and a biophysical model that is specific to the person, and typically simulates at least a part of the patient's anatomy, such as (part of) the patient's cardiovascular system, the patient's pulmonary system, the patient's digestive system, a metabolic process of the patient, and so on. Such a biophysical model may be developed from patient data, e.g. imaging data such as CT images, MRI images, ultrasound images, and so on. A typical workflow for creating and validating a 3D, subject-specific biophysical model is depicted in "Current progress in patient-specific modeling", by Neal and Kerckhoff, 1, 2009, Vol. 2, pp. 111-126.

Such a remote computer system 20 may be located or accessible in a health care environment such as a surgery, hospital or the like, from which a medical practitioner can remotely monitor the physical state of the person 10. Alternatively, such monitoring may be performed automatically such that a consult or procedure for the person 10 is only scheduled when his or her digital twin predicts the imminent occurrence of a critical medical condition or any other change in the physical condition of the person 10 that ideally requires the patient to be brought face to face with a health care professional. Moreover, the person 10 may be requested to undergo one or more controlled test based on the sensor data provided by the sensors 12, 14, 16 for the purpose of updating the digital twin as will be explained in further detail below.

The sensor data provided by the one or more sensors 12, 14, 16 to the computer system 20 hosting the digital twin through its processor arrangement 22 is used to update the digital twin such that the physiology of the patient 10 as monitored by the sensor data can be accurately simulated with the digital twin.

Figure 2:
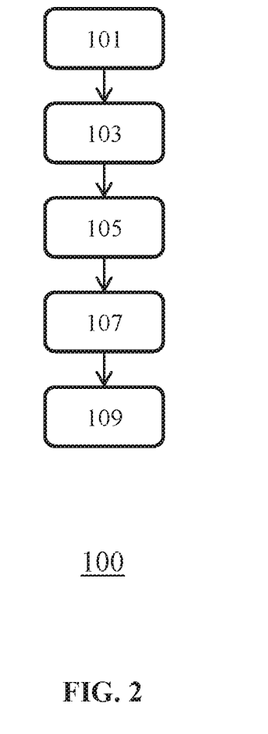
FIG. 2 is a flowchart of a method according to an embodiment.

An embodiment of a method 100 of the present invention is now explained with the aid of FIG. 2, which depicts a flowchart of the method 100. The method 100 may be implemented by the processor arrangement 22 of the computer system 20 or alternatively may at least in part be implemented by the processor arrangement 52 of the relay device 50. The method 100 starts in operation 101, after which the method 100 proceeds to operation 103 in which sensor data from the sensors 12, 14, 16 is collected over an extended period of time, e.g. several days, weeks or even months, such that the sensor data is likely to contain the full range of values that each parameter monitored with the sensors 12, 14, 16 can adopt. Such sensor data is likely to reflect a range of activities of the person 10 at different points in time during the extended time period that can affect the obtained parameter values. For example, physical exercise may increase the respiration rate and heart rate of the person 10, salt intake when dining out or certain types of social activities such as business meetings may increase the blood pressure of the person 10, and so on, or variations in the obtained parameter values may be related to a particular time of day. In addition, a psychological state, e.g. a state of mind, or the person 10 may have an impact on the observed parameter values. Therefore, in at least some embodiments the data collection in operation 103 is not limited to sensor data but may include data from which physical activities, e.g. social interactions and the psychological condition of the person 10 can be derived, such that a parameter value obtained at a particular point in time, e.g. a range of values obtained over a time interval coinciding with the social activity or psychological information, can be linked to this information. Such social activity or psychological information may be derived in any suitable manner. For example, the social activity information may be derived from an electronic diary of the person 10, whereas the psychological information may be derived from any suitable combination of sensors, such as brain activity sensors, blood pressure sensors and so on. Alternatively or additionally, the person 10 may personally provide such information, e.g. using a user interface coupled to the computer system 20 or the relay device 50, using speech recognition software, and so on.

It is further noted that the collected data with sensors 12, 14, 16 is not necessarily limited to physiological parameter data, but may also include environmental data from which the location and/or activity of the person 10 may be derived. Any suitable type of sensors may be used for this purpose, such as GPS sensors, altitude sensors, particulate matter sensors, temperature sensors and so on. Generally speaking, any type of environmental sensor that can provide environmental data that can affect a certain physiological parameter that is sensed for the person 10 may be used for this purpose. For example, an altitude meter may explain changes to a red blood cell count in the blood of the person 10, a wind meter may explain why during a heart rate pattern indicating physical exercise (e.g. cycling) the heart rate became more elevated than typical for the type of physical exercise and so on. Moreover, as previously mentioned the user may provide relevant information such as activity information, psychological state information and so on, using a user interface associated with any one of such sensors.

Upon receiving the sensor data and optional supplementary data in operation 103, the method 100 proceeds to operation 105 in which the received data is evaluated in order to generate a digital model of the person 10 based on the obtained parameter values and where applicable, the provided supplementary information. This digital model will also be referred to as the personalized parameter model of the person 10. This evaluation typically seeks to establish the dynamic behaviour of each sensed parameter during the extended monitoring period of the person 10. Such dynamic behaviour may include changes in the value of the sensed parameter over time, the rate of change of such a sensed parameter, changes in the value of the sensed parameter resulting from specified or assumed user behaviour, relationships between the changes in the values of different sensed parameters, the range of values adopted by such sensed parameters, that is, the end points of each of these ranges, and so on. It is noted that such end points may correspond with the values obtained for the relevant parameter with at least one of the sensors 12, 14, 16. Alternatively, at least one of the end points may be estimated based on an assumed actual state of the physiology as derived from the observed parameter values. For example, in case of the observed parameter values being indicative of the person 10 being in excellent physical shape, for instance based on the maximum heart rate of the person 10 during physical exercise, a resting heart rate value typical for persons in excellent physical shape of 50 BPM may be assumed, e.g. in a scenario in which the actual resting heart rate information is unavailable in the sensor data.

Generally speaking, the personalized parameter model contains parameter value evaluation information that is indicative of the actual state of the physiology of the person 10. For example, relationships between sensed parameters may be determined in this evaluation, that is, the interaction between certain parameters such as a change in respiration rate being linked to a change in heart rate for example, which relationships may also be captured in the personalized parameter model. Hence, the personalized parameter model typically comprises the established dynamic behaviour for each parameter observed with the sensors 12, 14, 16 over a defined monitoring period and may further comprise relationships between such parameters, as well as activity, environmental and/or psychological information associated with at least some of the parameter values at certain points in time, as explained above, based on which the actual state of the physiology of the person 1 can be estimated.

The personalized parameter model may be generated as a mathematical function that is able to represent data, or as a data model such as a convolutional neural network trained on the data received in operation 103, by using regression analysis of the data received in operation 103 and so on. Both approaches typically rely on the creation of a transfer function in which user behaviours are linked to the acquired sensor data, by building such a transfer function between set of inputs (e.g. corresponding to user behaviours), and outputs (e.g. corresponding to sensor data), or vice versa. In case of the personalized parameter model being based on a mathematical representation, the aim is to have a closed form equation, or finite element model that is able to generate a set of outputs, given a particular input. In case of the personalized parameter model based on a data driven approach, the connections between inputs and outputs are established using a convolutional neutral network or any other suitable supervised or unsupervised machine learning approach, such as support vector machines, logistic regression, decision trees, hierarchical clustering, and so on, which again can generate an output for a given input, although in this case the transfer functions typically cannot be represented in a closed form. The advantage of the mathematical approach is that if accurately constructed, this model is directly linked to the physiology and anatomy of the person 10, can be more easily understood, is simpler and faster, and is insensitive to data characteristics. The disadvantage of such a mathematical model is that it may be more difficult and sometimes impossible to construct, as it may require the collection of large amounts of data under well-defined conditions. In contrast, the advantage of the data driven model is that it is simpler to construct, although it may not be generalized and is highly sensitive to the available data.

In a preferred embodiment, the data in the personalized parameter model is clustered into a plurality of distinct clusters or non-overlapping sub-ranges during the generation of the personalized parameter model. Such clusters may be used to divide the data points in any suitable number of clinically relevant clusters, e.g. three or more clusters. For example, in case of a monitored heart rate, the data points may be clustered into a first cluster ranging from 60-90 BPM (normal heart rate), 90-130 BPM (moderately elevated heart rate) and 130-180 BPM (severely elevated heart rate), in which the distribution of the data points over the various clusters for instance provides lifestyle information about the person 10, which may be used to update the digital twin of the person 10 in a more informed manner. The values of individual parameters may be clustered in this manner, as well as the values of related parameters may be clustered together. Such clustering may serve a number of purposes. For instance, by distributing the observed data points over the defined clusters, an insight is provided into the lifestyle of the person 1. Such clusters may be considered as transfer functions between the lifestyle of the person 1 and the acquired sensor data. For example, if for the person 1, it is observed that 50% of collected heart rate data falls in a first cluster and the other 50% of this data falls in a second cluster, then a probabilistic function (for the digital twin) can be constructed that is able to generate heart rate values similar to the observed percentages. In addition, where the sensor data is supplemented with activity information, the activity can be used to associate observed parameter values with such an activity. For example, it can be derived either from the sensor data, e.g. from a time stamp, or from user-provided information that after the consumption of a (salty) meal, most of the data points captured with a heart rate sensor lie in a cluster indicative of an elevated heart rate, such that the personalized parameter model can capture this association. Such an association may subsequently be used to update the digital twin of the person 1 such that if an input of the digital twin is indicative of a higher salt intake, the digital twin would be more likely to generate an output capturing such a higher heart rate value.

The clustering of the various data values may be achieved in any suitable way, such as in an unsupervised procedure using clustering techniques such as hierarchical clustering, k-means clustering and so on. As such clustering techniques are well-known per se, this is not explained in further detail for the sake of brevity only.

Upon generation of the personalized parameter model in operation 105, the method 100 proceeds to operation 107 in which the personalized parameter model is made available for updating the digital twin of the person 10. This may involve transmitting the personalized parameter model from the relay device 50 to the computer system 20 over the data communication link 25 in case of the generation of the personalized parameter model on the relay device 50. Operation 107 may further involve storing the personalized parameter model on a data storage device such as the data storage device 30, for example in case of the generation of the personalized parameter model on the computer system 20 or upon receiving the personalized parameter model from the relay device 50. Upon completion of operation 107, the method 100 terminates in operation 109.

Figure 3:
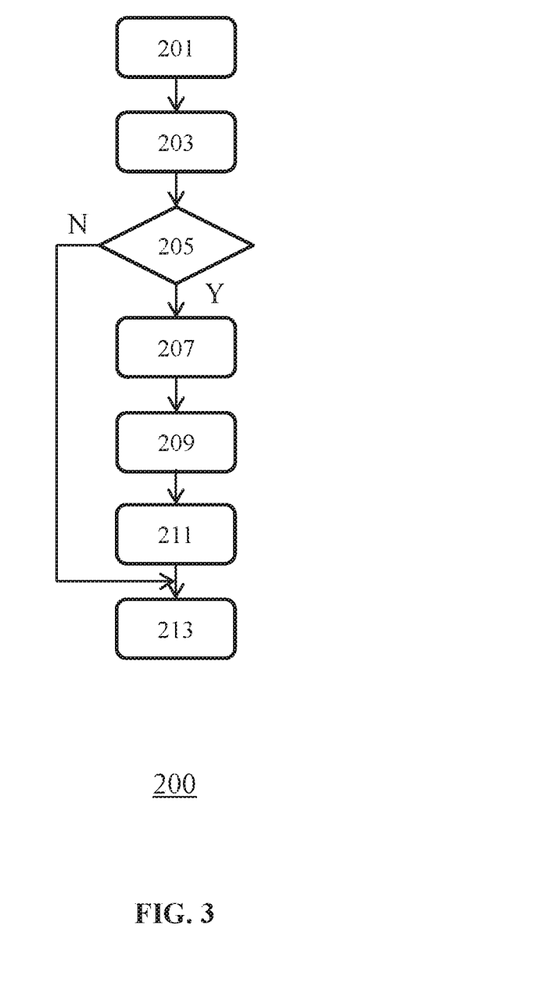
FIG. 3 is a flowchart of a method according to another embodiment.

FIG. 3 is a flowchart of a first embodiment of a method 200 for updating the digital twin of the person 10 using the personalized parameter model as generated with the method 100. The method 200 is typically executed by the processor arrangement 22 of the computer system 20. The method 200 starts in operation 201 after which the method 200 proceeds to operation 203 in which the personalized parameter model is obtained, e.g. retrieved from data storage device 30, received from relay device 50, and so on. Upon receiving the personalized parameter model in operation 203, the processor arrangement 20 in operation 205 compares the established dynamic behaviour of the parameter values in the personalized parameter model, e.g. the transfer functions between the lifestyle information of the person 1 and the observed parameter values, with previously assumed dynamic behaviour of these values, e.g. previously assumed transfer functions, on which the development of the digital model of the person 10 was based. In particular, such previously assumed dynamic behaviour of the sensed parameters as well as the assumed interactions between such parameters may have been used to define test protocols for establishing this dynamic behaviour in one or more controlled tests, that is tests or measurements performed in a controlled manner as previously explained in order to obtain accurate values of such parameters used by the digital model of the person 10. If it is decided in operation 205 that the parameter information contained within the personalized parameter model corresponds to the previously assumed parameter information, e.g. dynamic behaviour and/or transfer functions as previously explained, it may be concluded that the digital model of the person 10 is still up-to-date such that no further action is required and the method 200 may terminate in operation 213. On the other hand, if it is decided in operation 205 that there is a discrepancy between the parameter information contained within the personalized parameter model and the previously assumed parameter information, the method 200 proceeds to operation 207 in which the test protocols for obtaining the range of values for a parameter in a controlled test performed on the person 10 for which such a discrepancy has been determined is updated, such that the updates test or measurement procedure can capture the dynamic behaviour this parameter as indicated or predicted in the personalized parameter model.

For example, a previously established test protocol for the creation of a heart model of the person 10 may have required stress testing the person 10 such that the heart rate of the person 10 covered a range of 60-120 BPM. However, the personalized parameter model may have indicated through observation of the person 10 over the extended time period during his or her daily routines that variation in the heart rate of the person 10 covers a range from 60-180 BPM. It is reiterated that the end points of such a range may correspond to the observed values of the heart rate of the person 10 or at least one of these end points may have been estimated based on the observed values of the heart rate of the person 10. As another example, the settings for an imaging scan such as a CT scan may be optimized based on the information retrieved from the personalized parameter file. For instance, having CT data collected in different high-resolution (HR) conditions as derived from the personalized parameter file will improve CT imaging, thereby potentially enabling the calculation of more accurate and representative digital model of the person 10 having improved risk prediction capabilities. For example, if it is observed from the personalized parameter model that most of the heart rate values of the person 10 are in a severely elevated heart rate cluster and normal heart rate model, it is important that the CT scans are performed when the person 10 has normal heart rate and when the user has a severely elevated heart rate such as to ensure that a representative digital model can be constructed for the person 10. This therefore deviates from common practice in which the quality of the captured CT image is taken to decide whether satisfactory scan results have been obtained, without ensuring that different CT images are captured under the conditions the person 10 has different (characteristic) heart rate values.

This information may be used to update the test protocol for determining the heart rate of the person 10 by testing the person 10 in accordance with the updated test protocol in a controlled test environment such as in a medical facility on the guidance of medical professionals in order to reproduce the dynamic behaviour of this parameter as well as interrelations between different parameters as previously explained. To this end, the person 10 may be subjected to such a controlled test, with the processor arrangement 20 processing the test result data in operation 209 and updating the digital model with the thus processed up-to-date test result data in operation 211 before terminating in operation 213. For example, in case of a personalized parameter model of the person 10 indicating a given heart rate distribution over the defined sub-ranges or clusters of the heart rate in which the heart rate of the user 10 predominantly falls in a particular cluster, the controlled test may be designed such that the heart rate of the person 10 is targeted to predominantly fall in this particular cluster. As another example, a specific relation between two sensors readings may have been established in the personalized parameter model, such as a significant increase in heart rate when the altitude at which the person 10 resides increases more than 500 m within 2 hours. Hence, the controlled test protocol may simulate such altitude change effects (e.g. by reducing the oxygen concentration in a gas mixture provided to the person 10 through a breathing mask), while collecting high-quality heart rate data. Such data would make the digital twin of the person 10 more representative of his or her lifestyle, and therefore more useful when evaluating the actual physiological state, and predicting the future physiological state of the person 10.

Operation 209 may further comprise a verification of the thus obtained test result to determine if the captured parameter values correspond to the expected parameter values from the personalized parameter model, such that upon this verification highlighting a non-trivial difference between the captured parameter values and the expected parameter values, the test protocol may be adjusted accordingly and the test repeated in accordance with this adjusted test protocol until the captured parameter values sufficiently correspond to the expected parameter values, after which the method 200 may proceed to operation 211.

Figure 4:
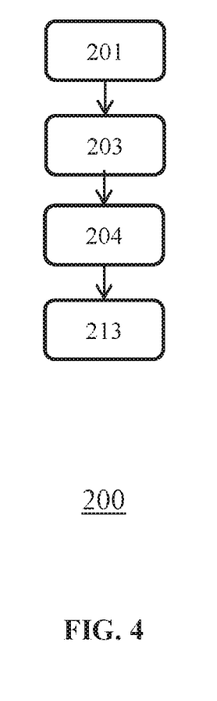
FIG. 4 is a flowchart of a method according to yet another embodiment.

The above embodiment of method 200 for updating the digital model of the person 10 is particularly suitable where the established parameter values with the sensors 12, 14, 16 cannot be used as direct input into the digital model of the person 10, for example because the sensor data is unreliable, e.g. noisy or incomplete, incompatible, e.g. heart rate data where the digital model requires ECG data as input or impermissible for use as such direct inputs, e.g. where the owner of the IP rights on the relay device 50 prohibits the reuse of such data in certain application domains. However, in an alternative embodiment of the method 200, a flowchart of which is depicted in FIG. 4, the sensor data as contained in the personalized parameter model is used as a direct input into the digital model of the person 10. This for instance may be desirable where the data is difficult to collect under controlled test conditions, e.g. because the required variability in the data values an only be obtained by monitoring over a prolonged period of time, or where the monitoring of longitudinal feature changes is desirable. It furthermore may be desirable to test the robustness of the digital model of the person 10 for real-life conditions, as the state of mind of the person 10 when subjected to tests in a medical facility is likely to be different, i.e. more stressed, than his or her state of mind during daily life outside such a medical facility. For example, a parameter such as a resting heart rate can be more accurately determined outside such controlled test environments as the person 10 is more relaxed within his or her familiar environment.

In this embodiment of the method 200, after obtaining the personalized parameter model in operation 203, the method 200 proceeds to operation 204 in which the sensor data is used to directly update the digital model of the person 10, e.g. by implementing derived dynamic behaviour of the parameter values and/or derived transfer functions in the personalized parameter model into the digital model, or to produce simulation conditions or algorithms such as transfer functions for the digital model that, upon simulating the lifestyle of the person 10, can accurately reproduce the dynamic behaviour of the sensed parameters as captured in the personalized parameter model. This for example may involve computing the updated digital model using data mining techniques such as deep learning, e.g. using convolutional neural networks. In addition or as an alternative, the sensor data may be used to test and validate the digital model. For example, a simulation run corresponding to the period of time over which the sensor data in the personalized sensor model has been acquired may be performed with the digital model to determine if the digital model can reproduce the sensor data with a satisfactory degree of accuracy. For example, in case of a haemodynamic model, it may be tested if this model can reproduce the blood pressure values of the person 10 as captured in the sensor data. If this is not the case, the digital model can be updated, e.g. using machine learning techniques as previously mentioned, in order to produce a digital model that can reproduce the observed sensor values with greater accuracy.

Figure 5:
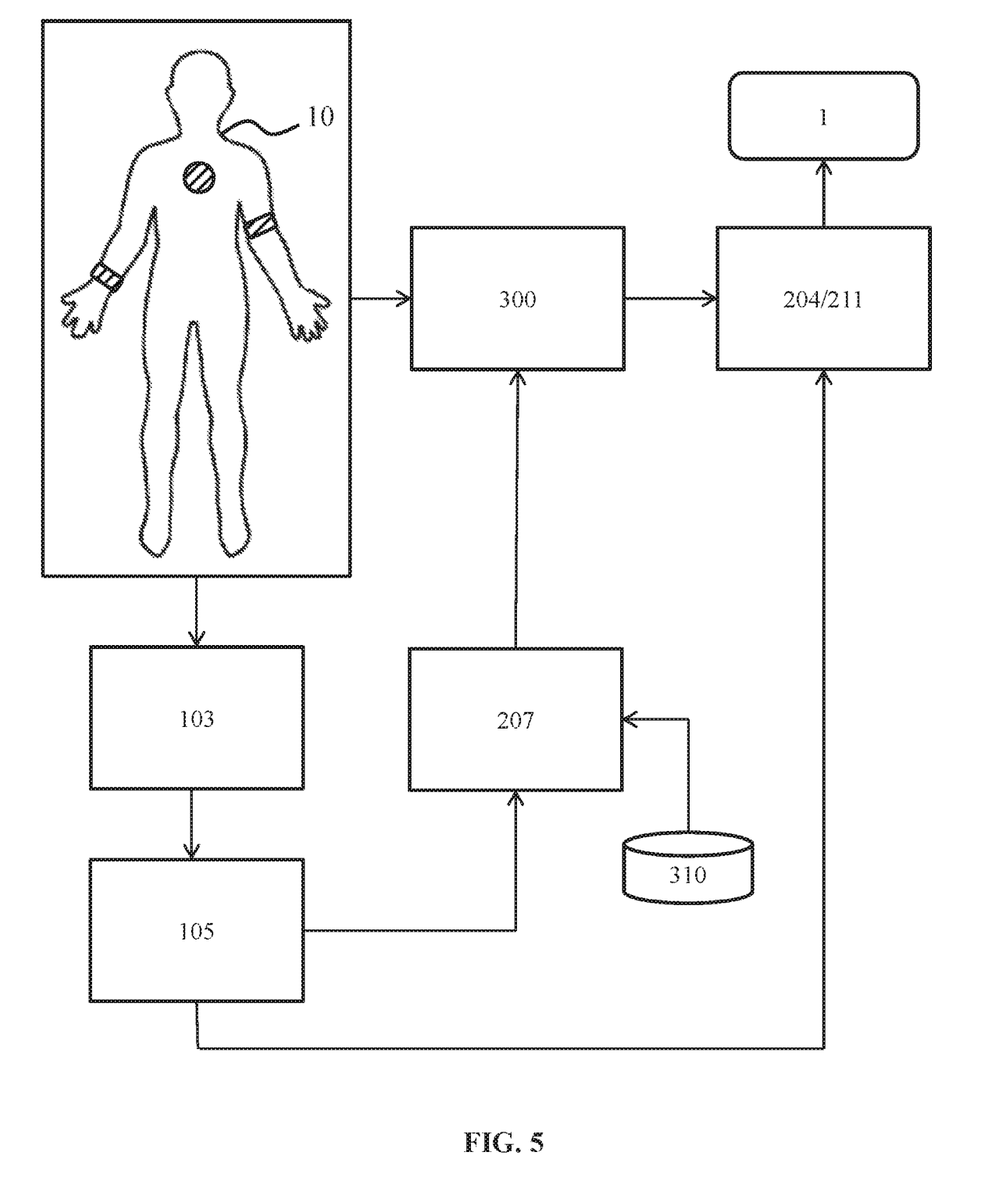
FIG. 5 schematically depicts an overview of various example embodiments of a method according to the present invention.

FIG. 5 schematically depicts a use case model that reflects how the embodiments of the methods 100, 200 of the present invention may be implemented. The person 10 is monitored with sensors 12, 14, 16 in his or her daily life over an extended time period as previously explained, e.g. to obtain a full range of data values with sufficient statistical relevance as guaranteed by the duration of the monitoring time period. This monitoring is reflected by operation 103 of method 100. From this completed set of monitoring data, the personalized parameter model may be built in operation 105 of method 100 as previously explained. The personalized parameter model may be directly used for updating the digital twin, as symbolized by operation 204 of method 200 as described above.

Alternatively or additionally, the personalized parameter model may be used to update the test protocol of one or more controlled tests in which the monitored parameters or parameters related to the monitored parameters may be acquired in previously described operation 207, e.g. by accessing a test protocol database 310 to retrieve the test protocol that ensures that when the controlled test is performed on the person 10 in operation 300, the resulting test data will fully cover the range of values as captured in the personalized parameter model. The thus obtained test data may be used to update the digital model 10 as symbolized by operation 211 of the method 200, e.g. using machine learning techniques as previously explained, or by altering an anatomical model of the person 10 based on imaging data acquired in test process 300, for example. Consequently, an updated digital model 1 may be produced that more accurately mimics the physiology of the person 10 during his or her daily routines.

Figure 6:
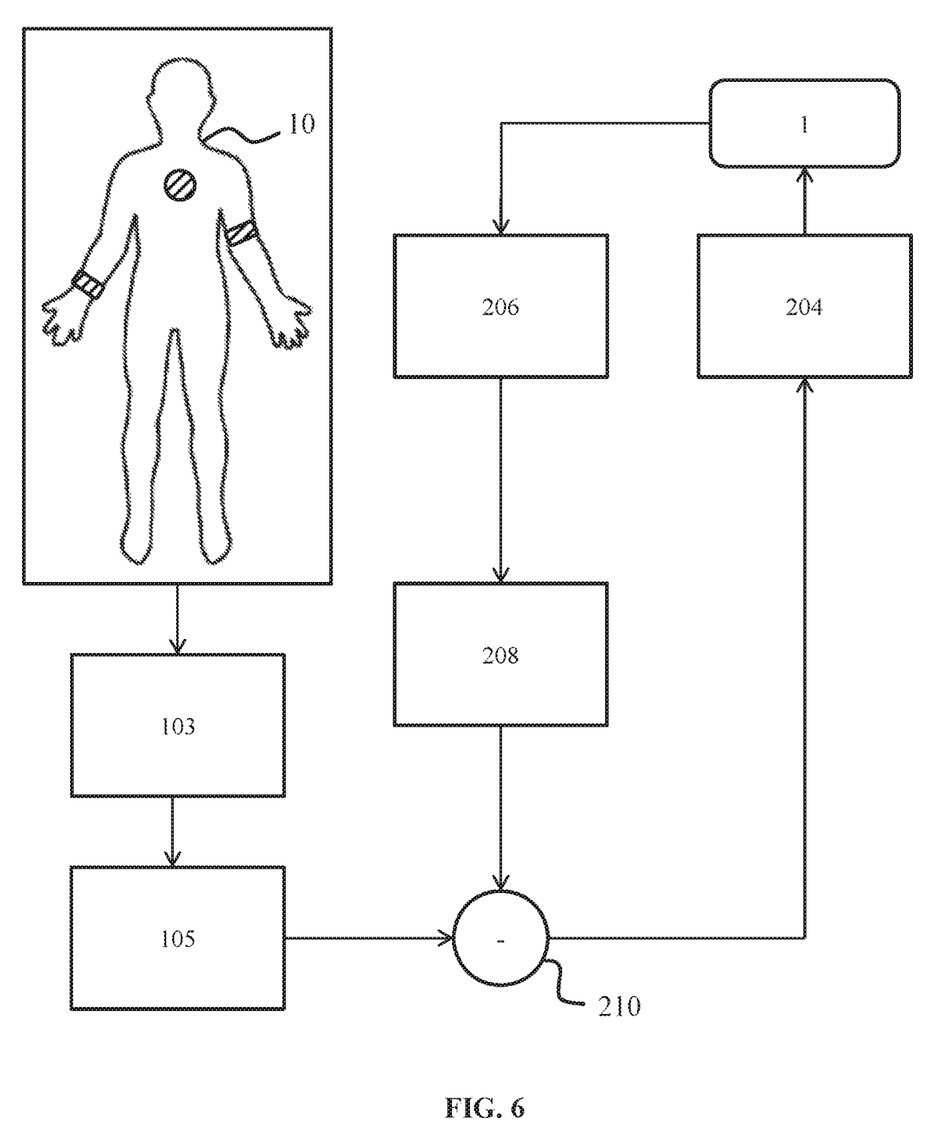
FIG. 6 schematically depicts an aspect of a method according to an example embodiment.

A further refinement of the method 200 in which the digital model is directly updated with the personalized parameter model is depicted by the flowchart of FIG. 6. In this embodiment, after updating the digital model, a simulation is run with the updated digital model 1 in operation 206. This simulation simulates the extended time period over which the sensor data captured in the personalized parameter model was acquired and generates simulated sensor data based on which a further personalized parameter model is generated in operation 208. This further personalized parameter model is generated in essentially the same manner as the personalized parameter model, or corresponding part thereof in case the digital model 1 is incapable of generating a further personalized parameter model covering the full scope of the personalized parameter model. In such a scenario, the simulated sensor data may be augmented with real-life sensor data, e.g. in case of simulated heart rate data, this data may be augmented with real-life stress information for the person 10, as the digital model 1 may be incapable of generating such stress data. The further personalized parameter model can be used as an indicator of the improved accuracy of the updated digital twin 1. To this end, in operation 210 a difference or residual between the personalized parameter model or relevant part thereof and the further personalized parameter model is determined to assess the accuracy of the updated digital twin 1, and in case of a non-negligible difference or residual, this difference or residual optionally may be fed back into the machine learning algorithm for updating the digital twin as represented by operation 204 such that the digital twin may be iteratively improved based on the determined difference or residual between the further personalized parameter model and the personalized parameter model or relevant part thereof.

For example, in case of a data-driven clustered personalized parameter model, a histogram of the data distribution over the various clusters as well as an estimation of the probability density function from the histogram may be produced by the computer system 20. As an example, the updated digital twin 1 may simulate a range of heart rate values based within a same range of VO2 max (maximum oxygen absorption rate) as present in the real life data. In case the further personalized parameter model generated from the simulated heart rate data differs from the data in the personalized parameter model, e.g. because the histogram generated from the further personalized parameter model indicates that the updated digital twin 1 fails to correctly reproduce low heart rate values, this information may be used to further update the digital twin, e.g. by changing the digital twin model, by collecting more data, e.g. with the sensors 12, 14, 16 and/or changing the training algorithm of the digital twin.

For example, in a scenario where there are several settings of the digital twin that can be tuned (e.g. tissue perfusion setting), by using the residual signal as a feedback, the settings of the digital twin can be tested with different values, and the settings that result in the lowest residual error may be selected to be used as default settings in the updated digital twin 1 of the person 10. By using such a residual minimization algorithm an exhaustive search for the optimized fitting values can be performed. This of course is heavily dependent on the reliability of the real-life data in the personalized parameter model, as in case of unreliable real-life data the optimization of the digital model is unlikely to be useful, and may instead reduce the accuracy of such a model.

Figure 7:
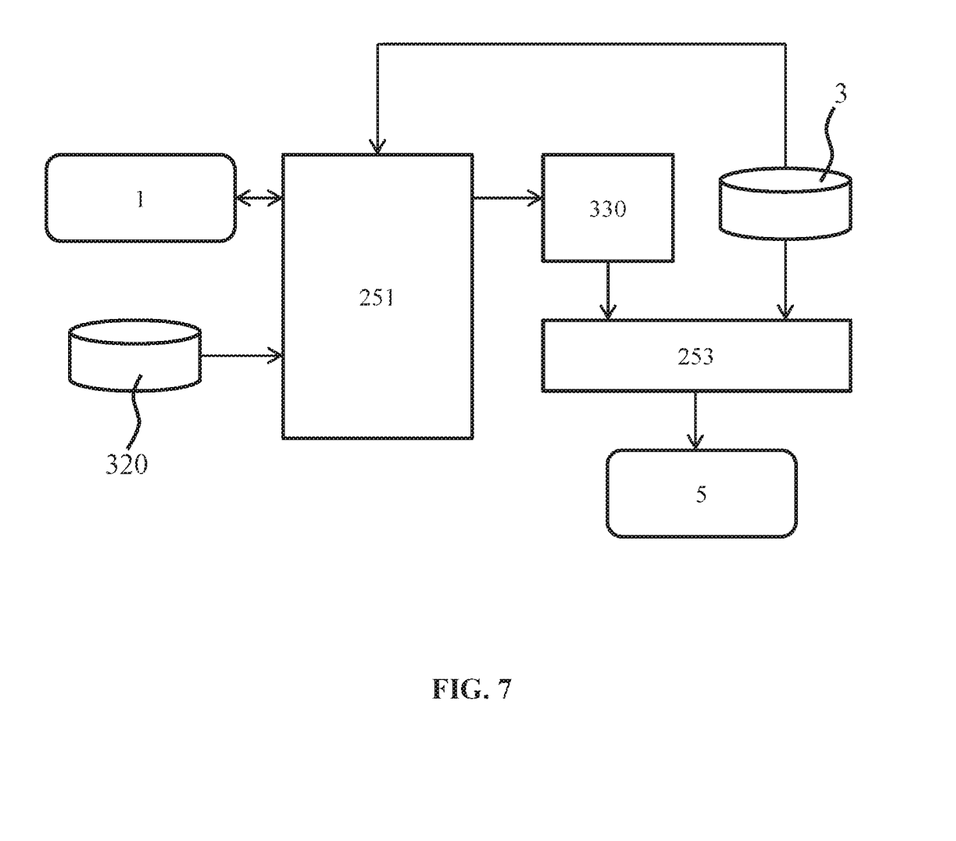
FIG. 7 schematically depicts another aspect of a method according to an example embodiment.

In an embodiment, the evaluation of the personalized parameter model may be leveraged to develop a behavioural model for the person 10. Such a behavioural model typically comprises a list of behaviours that cause certain changes (trends) in one or more of the parameter values obtained with the sensors 12, 14, 16. This therefore can be seen as a higher level representation of the data relating to the person 10, as it is not necessarily presented in the form of parameter values (alone), but instead shows a correlation between certain types of behaviours and the impact this behaviour has on one or more observed parameter values with one or more of the sensors 12, 14, 16.

This process is explained in more detail with the aid of FIG. 7, which depicts a flowchart of such an example process. The processor arrangement 22 of the computer system 20 may access a knowledge database 320 in which behaviours known to affect a physiological parameter value are stored. The processor arrangement 22 may compile a list of behaviours retrieved from the knowledge database 320 that are known to affect the value of a physiological parameter of interest, e.g. a physiological parameter monitored with one of the sensors 12, 14, 16. For example, in case of the digital twin 1 comprising a haemodynamic model of the person 10, the processor arrangement 22 may retrieve behaviours from the knowledge database 320 that can affect parameter values associated with such a haemodynamic model, such as for example (changes in) salt intake, (changes in) alcohol consumption, (changes in) physical activity, and so on.

In operation 251, the processor arrangement 22 may run a simulation with the digital model 1 to determine which of the listed behaviours are relevant to the person 10. Such a simulation typically uses at least some of the determined behaviours as some input to the digital model, with at least one of the parameter data in the personalized parameter model 3 and historical parameter data, e.g. as obtained from earlier versions of the personalized parameter model 3 or as obtained from earlier controlled tests on the person 10, as optional further input data of the digital model 1. However, running the simulation without such optional further input data has the advantage that the impact of certain behaviours can be estimated even in the absence of such behaviours in the historical data or the data of the personalized parameter model 3.

The simulation results are also evaluated in operation 251 to determine those behaviours from the set of behaviours that have caused a significant or relevant change in the output (state) of the digital model. Such an evaluation may be performed by the computer system 20 or alternatively may be performed at least in part by one or more trained medical practitioners to determine which behaviours are worth monitoring. In this manner, a subset of behaviours that can have an effect on a physiological state of the person 10 can be determined. This for example may be achieved by identifying trends in the data within the digital model 1 and matching these trends with known trends for any of the listed relevant behaviours. This may be further verified using information in the personalized parameter model 3 that is indicative of a certain type of behaviour activity of the person 10, such as information provided by environmental sensors, electronic diary information, information provided by the person 10, and so on. In this manner, the processor arrangement 22 may build a list 330 of behaviours relevant to the person 10.

In operation 253, the relevance of each of these behaviours may be quantified by evaluation of the data provided by the personalized parameter model 3. This operation is of course particularly relevant where the simulation in operation 251 was performed without using the parameter data in the personalized parameter model 3, as otherwise operation 253 may form part of the evaluation performed in operation 251. This quantification for example may involve quantifying the magnitude of any observed trends in this data corresponding to a certain type of behaviour such that the potential impact of this behaviour on the health of the person 10 can be quantified with the digital model 1. For example, in case of the salt intake of the person 10, the salt intake may be classified as 'insignificant', 'moderate' or 'significant' based on the magnitude of the change to the blood pressure of the person 10 as observed with a blood pressure sensor attached to the person 10. In this manner, a user behaviour model 5 may be built, in which recognized and quantified user behaviours that have a potential impact of the person's health are collected. In this manner, the computer system 20 may determine whether certain behaviours should be avoided, sustained or encouraged. Such quantification of recognised behaviours may further involve simulations with the digital twin 1. For example, if it is determined that the person's salt intake increased as a result of certain social interactions, a simulation with the digital twin 1 using the increased salt intake as an input parameter may be run to determine which physiological parameters will change and in which manner. This way, the set of relevant physiological parameters affected by such behaviour as well as their expected changes resulting from such behaviour can be estimated with the digital twin 1.

Such a user behavior model 5 may be used to generate a guidance or coaching system of the person 10 that can interact with the person 10 in order to provide the person 10 with lifestyle guidance information in order to help the person 10 maintain a healthy lifestyle, or at least manage the impact of certain behaviours on the health of the person. Such guidance information may be presented to the person 10 in any suitable form, such as for example in the form of an electronic (media) message that may be sent to an electronic device registered to the person 10, such as a smart phone, email account, and so on.

For example, where the user behaviour model 5 as identified that interaction of person 10 with a particular other person leads to changes in the sensor data are indicative of significantly increased salt and alcohol intake, e.g. because of person 10 regularly dining out with this other person, the guidance or coaching system may message the person 10 to advise the person 10 to take caution when meeting this other person. Of course, this example use case presumes that the personalized parameter file 3 based on which the guidance advice has been generated contains information that links the increased salt and alcohol intake to the aforementioned social activities of the person 10, e.g. from electronic diary entries or the like. In the absence of such activity information, the guidance message sent to the person 10 may be more generic in nature, such as advising the person 10 to moderate salt and/or alcohol intake. The lifestyle guidance advice may be produced based on the evaluation of any personalized parameter model 3, such as a subsequently generated any personalized parameter model.

As another example, the data in the personalized parameter file 3 may highlight that meetings between the person 10 and a specific other person lead to an increased blood pressure for the person 10, and that the person 10 has a tendency towards higher blood pressures at the end of the (working) day, where the simulations with the digital model 1 have indicated that such higher blood pressures are detrimental to the person 10. Therefore, this knowledge may be leveraged by the guidance or coaching system in generating an electronic message to the person 10 advising him or her to meet with this other person during morning hours and to limit the duration of such meetings, such as to minimize the impact of such hypertensive events as estimated with the digital model 1. The guidance or coaching system may further include guidance as to how to counter such potentially health-adverse events, e.g. prescribing paced breathing exercises following a stressful meeting in order to reduce blood pressure, with the beneficial effect of such exercises having been established through simulation with the digital model 1 prior to prescription Similarly, where the data in the personalized parameter model 3 shows that certain types of activities have a positive effect on the values of certain monitored parameters, the guidance or coaching system may generate an electronic message for the person 10 encouraging him or her to frequently engage in such beneficial activities.

Embodiments of the present invention are applicable to the management of any type of digital twin used as a biophysical model for at least a part of the anatomy of a person 10, such as a patient. Some non-limiting examples include the monitoring of cardiovascular diseases, in which social interactions of the person 10 causing stress or relaxation can strongly influence the state of the cardiovascular system, e.g. through blood pressure changes and blood vessel contraction/expansion, mother and (unborn) child care in which social interactions of the pregnant mother can influence prenatal development, such as through nutrition and blood pressure of the mother, oral healthcare in which social interactions can be positively influenced by good oral health, which may be controlled through nutrition and oral care, and skin care, as it is known per se that social interactions influence skin health and vice versa. Many other examples will be immediately apparent to the skilled person.

The above described embodiments of the method 100 executed by the processor arrangement 22 may be realized by computer readable program instructions embodied on a computer readable storage medium having, when executed on a processor arrangement 22 of a computer system 20, cause the processor arrangement 22 to implement any embodiment of the method 100. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like. The computer readable storage medium may be an Internet-accessible service from which the computer readable program instructions may be obtained. In an embodiment, the computer system 20 is adapted to retrieve the computer readable program instructions from such a computer readable storage medium and to create a new computer readable storage medium by storing the retrieved computer readable program instructions in a data storage arrangement 30 accessible to the computer system 20, e.g. in a memory device or the like forming part of the computer system 20.

The computer system 20 may be adapted to implement the embodiments of the method 100 by hard-coding the various steps and operations of the method 100 into the processor arrangement, e.g. by the provision of one or more ASICs. designed for this purpose. Alternatively, the computer system 20 may comprise the aforementioned computer program product communicatively coupled to the processor arrangement 22 such that the processor arrangement 22 may include one or more general purpose processors capable of executing the computer readable program instructions embodied thereon.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A method of providing a personalized parameter model of at least part of the internal physiology of a person carrying a set of sensors with a computer system comprising a processor arrangement, the method comprising, with said processor arrangement:
receiving sensor data from said set of sensors with a communication interface over a defined period of time, the sensor data from each sensor representing a parameter relevant to an actual internal physiological state of the person;
evaluating the received sensor data from each sensor to define a personalized parameter model, said model including an evaluated dynamic behaviour of the values of each parameter observed with said sensors over the defined period of time, and wherein evaluating the received sensor data from each sensor to define the personalized parameter model further comprises: (i) dividing the values of at least some of the parameters observed with said sensors over the defined period of time into a plurality of sub-ranges; (ii) generating a distribution of the values of the at least some of the parameters observed with said sensors over the defined period of time across the plurality of sub-ranges; and (iii) including said distribution in the personalized parameter model; and
providing the defined personalized parameter model for updating a digital model of said person.

2. The method of claim 1, wherein evaluating the received sensor data from each sensor to define the personalized parameter model further comprises:
determining the end points of a parameter value range for each parameter based on the values of each parameter observed with said sensors over the defined period of time; and
including said determined end points in the personalized parameter model.

3. The method of claim 1, wherein evaluating the received sensor data from each sensor to define the personalized parameter model comprises:
determining one or more relationships between two or more of said parameters observed with said sensors over the defined period of time from the evaluated dynamic behaviour of the values of said parameters and
including the determined one or more relationships in the personalized parameter model.

4. The method of claim 1, further comprising:
receiving at least one of activity information and psychological information for a particular point in time for said person;
associating received sensor data acquired at that particular point in time with said received information; and
including said associations in the personalized parameter model.

5. A method for updating a digital model of a person carrying a set of sensors with a computer system comprising a processor arrangement, wherein:
each sensor in said set of sensors is arranged to collect sensor data representing a parameter relevant to an actual internal physiological state of the person; and
the digital model is a parameterized model based on at least some of the parameters sensed with said set of sensors;
the method comprising, with said processor arrangement:
obtaining the personalized parameter model provided in accordance with the method of claim 1; and
updating the digital model using the personalized parameter model.

6. The method of claim 5, wherein said updating the digital model using the personalized parameter model comprises:
comparing the evaluated dynamic behaviour of each parameter observed with the set of sensors with a previously assumed dynamic behaviour of said parameter on which the digital model is based, and when the evaluated dynamic behaviour of at least one parameter observed with the set of sensors is different to the previously assumed dynamic behaviour of said parameter:
updating a test protocol for obtaining the evaluated dynamic behaviour of said parameter in a controlled test performed on the person; and
updating the digital model with the evaluated dynamic behaviour of said parameter as obtained from said person in said controlled test.

7. The method of claim 5, wherein updating the digital model using the personalized parameter model comprises directly updating the digital model with the evaluated dynamic behaviour of said parameter observed with a sensor from the set of sensors.

8. The method of claim 5, further comprising validating the digital model using the evaluated dynamic behaviour of at least one of the parameters observed with the set of sensors.

9. The method of claim 5, further comprising:
generating a further personalized parameter model comprising a further dynamic behaviour of the sensed parameters with the updated digital model;
comparing the further personalized parameter model with the personalized parameter model; and
when the further personalized parameter model differs from the personalized parameter model, further updating the digital model based on said determined difference.

10. The method of claim 5, further comprising:
determining a set of behaviours of a person that each cause a trend in a value of at least one parameter on which the digital model is based;
running a simulation with the digital model using the behaviours in said set and optionally at least one of historical parameter data and parameter data from the personalized parameter model associated with behaviours in said set as input data;
evaluating said simulation; and
generating a behavioural model of the person comprising each of the behaviours in said set identified by the simulation evaluation as relevant to the person.

11. The method of claim 10, further comprising:
receiving a subsequent personalized parameter model based on a subsequently determined range of values for each parameter observed with said set of sensors;
evaluating the received subsequent personalized parameter model for a trend in the sensor data of the subsequent personalized parameter model that corresponds to one of the behaviours in the behavioural model with the digital model; and
generating an electronic message for the person when the evaluation of the received subsequent personalized parameter model identifies a trend in the sensor data of the subsequent personalized parameter model that corresponds to one of the behaviours in the behavioural model with the digital model, said electronic message containing information for the user pertaining to the identified behaviour, optionally wherein said information is further based on received activity information and/or psychological information for said person that is relevant to the identified trend in the sensor data.

12. A computer program product for a computer system comprising a processor arrangement under control of said processor arrangement, the computer program product comprising a non-transitory computer readable storage medium having computer readable program instructions embodied therewith for, when executed on the processor arrangement, cause the processor arrangement to implement the method of claim 1.

13. A computer system comprising a processor arrangement, wherein the processor arrangement is adapted to implement the method of claim 1.

14. The computer system of claim 13, further comprising a computer program product communicatively coupled to the processor arrangement.

* * * * *